United States Patent
Gyurik et al.

(10) Patent No.: US 7,989,419 B2
(45) Date of Patent: *Aug. 2, 2011

(54) INSULIN COMPOSITION

(75) Inventors: Robert J. Gyurik, Exeter, NH (US); Carl Reppucci, North Andover, MA (US)

(73) Assignee: CPEX Pharmaceuticals, Inc., Exeter, NH (US)

( * ) Notice: Subject to any disclaimer, the term of this patent is extended or adjusted under 35 U.S.C. 154(b) by 564 days.

This patent is subject to a terminal disclaimer.

(21) Appl. No.: 11/811,169

(22) Filed: Jun. 8, 2007

(65) Prior Publication Data

US 2008/0045446 A1    Feb. 21, 2008

Related U.S. Application Data

(60) Provisional application No. 60/811,913, filed on Jun. 8, 2006.

(51) Int. Cl.
*A61K 38/28* (2006.01)
(52) U.S. Cl. ......................................................... 514/5.9
(58) Field of Classification Search .................. None
See application file for complete search history.

(56) References Cited

U.S. PATENT DOCUMENTS

| | | | |
|---|---|---|---|
| 5,023,252 | A | 6/1991 | Hseih |
| 5,731,303 | A | 3/1998 | Hsieh |
| 7,112,561 | B2 * | 9/2006 | Gyurik et al. .................... 514/3 |
| 7,244,703 | B2 * | 7/2007 | Gyurik et al. .................... 514/2 |
| 2004/0176476 | A1 * | 9/2004 | Gyurik ........................ 514/772.6 |
| 2005/0123592 | A1 * | 6/2005 | Gyurik et al. .................... 424/448 |
| 2005/0232867 | A1 * | 10/2005 | Gyurik et al. .................... 424/45 |
| 2007/0010425 | A1 * | 1/2007 | Gyurik et al. .................... 514/3 |
| 2007/0265191 | A1 * | 11/2007 | Gyurik et al. .................... 514/2 |
| 2008/0045446 | A1 * | 2/2008 | Gyurik et al. .................... 514/3 |
| 2008/0045447 | A1 * | 2/2008 | Gyurik et al. .................... 514/3 |
| 2008/0107735 | A1 * | 5/2008 | Gyurik et al. .................... 424/486 |
| 2009/0156464 | A1 * | 6/2009 | Gyurik et al. .................... 514/3 |
| 2009/0286715 | A1 * | 11/2009 | Gyurik ............................ 514/3 |

OTHER PUBLICATIONS

Heinemann et al. "Time-Action Profile of the Long-Acting Insulin Analog Insulin Glargine (HOE901) in Comparison With Those of NPH Insulin and Placebo," Diabetes Care 23:644-649, 2000.*
FDA label for LANTUS (insulin glargine) printed Dec. 4, 2009.*
Berg et al. (Biochemistry 5th Ed. 2002, Appendix: pKa Values of Some Acids).*
Electronic Supplementary Material for CrystEngComm, The Royal Society of Chemistry (2005, Supplementary material—list of pharmaceutically acceptable acids).*
Joint FAO/WHO Expert Committee on Food Additives (JECFA) entry on sorbitan monolaurate printed Dec. 4, 2009.*
Hua et al., "Mechanism of Insulin Fibrillation: The Structure of Insulin Under Amyloidogenic Conditions Resembles a Protein-Folding Intermediate," J. Biol. Chem. May 14, 2004, vol. 279, No. 20; pp. 21449-21460.
Nielsen et al., "Effect of Environmental Factors on the Kinetics of Insulin Fibril Formation: Elucidation of the Molecular Mechanism," Biochemistry. 2001, vol. 40, No. 20; pp. 6036-6046.
Nielsen et al., "Probing the Mechanism of Insulin Fibril Formation with Insulin Mutants," Biochemistry. 2001, vol. 40, No. 28; pp. 8397-8409.
International Search Report for international application No. PCT/US07/13512 issued by the International Searching Authority mailed on May 27, 2008.
Written Opinion for international application No. PCT/US07/13512 issued by the International Searching Authority mailed on May 27, 2008.

* cited by examiner

*Primary Examiner* — Christina Bradley
(74) *Attorney, Agent, or Firm* — Michael A. Davitz

(57) ABSTRACT

Pharmaceutical compositions for nasal administration to humans, or to warm-blooded animals, comprise: (A) a therapeutically effective amount of insulin; (B) a permeation enhancer; and (C) a liquid carrier; the compositions being further comprised of, or characterized by, any, or each, of: (D) a combination of non-ionic surfactants; wherein the combination of non-ionic surfactants comprises: (i) at least one fatty acid ester of a sugar or sugar alcohol and (ii) at least one pegylated fatty acid ester of a sugar or sugar alcohol; (E) an acidic pH, but no greater than a pH of 4.5; and (F) an osmolality of <200 mOsmol/Kg H2O.

12 Claims, 2 Drawing Sheets

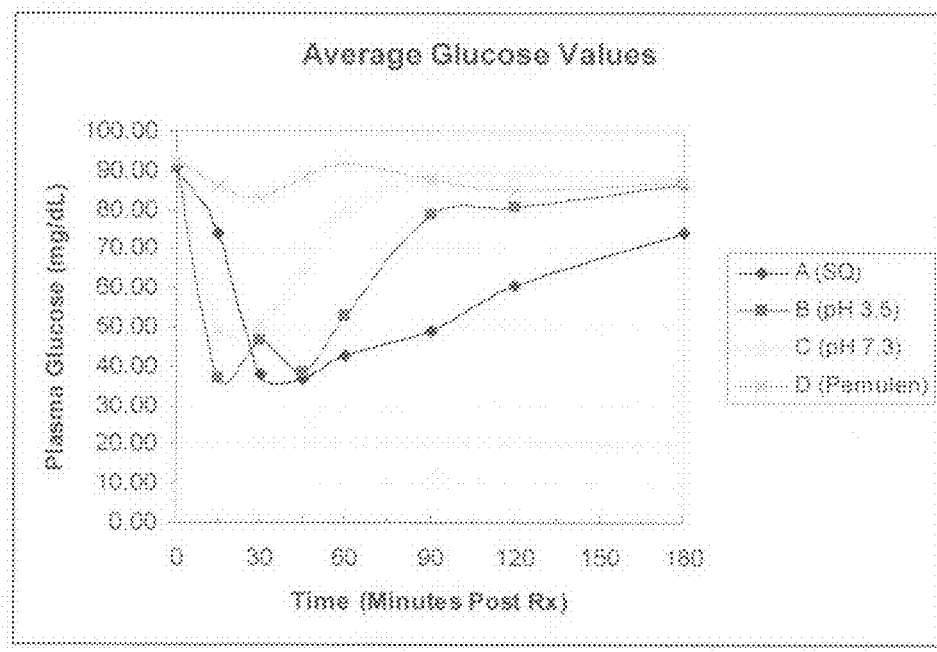
Figure 1. Average Glucose Values (n=8)

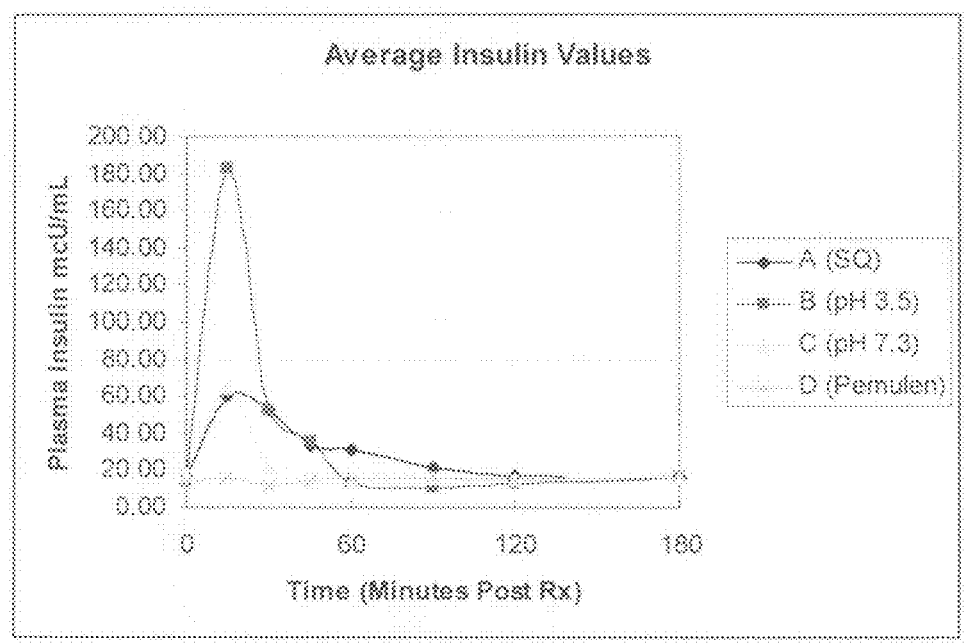
Figure 2. Average Insulin Values

INSULIN COMPOSITION

This application claims priority to U.S. Provisional Application Ser. No. 60/811,913, filed Jun. 8, 2006, the disclosures of which are hereby incorporated by reference in their entireties.

This invention relates to compositions and methods for delivery of insulin, and more particularly for the delivery of insulin other than by injection, across skin, membranes of various body cavities such as ocular, nasal, oral, buccal, anal, rectal, vaginal, and blood brain barrier and like membranes.

Insulin is generally used to treat patients that suffer from diabetes. In general, insulin is delivered to a patient by injection.

U.S. Pat. No. 5,023,252 describes a composition for delivery of insulin by a route other than by injection. More particularly, such patent describes the use of compositions that include permeation enhancers for delivery of insulin through skin and membranes of body cavities without requiring an injection.

The present invention is directed to an improvement in such compositions and the use thereof.

BRIEF DESCRIPTION OF THE DRAWINGS

FIG. 1 depicts the average plasma glucose values at various time points after the administration of formulations A, B, C or D.

FIG. 2 depicts the average plasma insulin values at various time points after the administration of formulations A, B, C or D.

In accordance with an embodiment of the invention, there is provided a pharmaceutical composition for nasal administration to humans, or to warm-blooded animals, comprising: (A) a therapeutically effective amount of insulin, (B) a permeation enhancer, (C) a liquid carrier, and (D) a combination of non-ionic surfactants; wherein the combination of non-ionic surfactants comprises: (i) at least one fatty acid ester of a sugar or sugar alcohol and (ii) at least one pegylated fatty acid ester of a sugar or sugar alcohol.

In accordance with another embodiment of the invention, there is provided a pharmaceutical composition for nasal administration to humans, or to warm-blooded animals, comprising: (A) a therapeutically effective amount of insulin, (B) a permeation enhancer, (C) a liquid carrier, and (D) a combination of non-ionic surfactants; wherein the combination of non-ionic surfactants comprises: (i) at least one fatty acid ester of a sugar or sugar alcohol and (ii) at least one pegylated fatty acid ester of a sugar or sugar alcohol; and wherein the composition is at an acidic pH, but no greater than a pH of 4.5.

In accordance with another embodiment of the invention, there is provided a pharmaceutical composition for nasal administration to humans, or to warm-blooded animals, comprising: (A) a therapeutically effective amount of insulin, (B) a permeation enhancer, and (C) a liquid carrier; wherein the osmolality of the composition is <200 mOsmol/Kg H2O. Preferably the osmolality of the composition is <150 mOsmol/Kg H2O.

In accordance with another embodiment of the invention, there is provided a pharmaceutical composition for nasal administration to humans, or to warm-blooded animals, comprising: (A) a therapeutically effective amount of insulin, (B) a permeation enhancer, and (C) a liquid carrier; wherein the osmolality of the composition is <200 mOsmol/Kg H2O; and wherein the composition is at an acidic pH, but no greater than a pH of 4.5. Preferably the osmolality of the composition is <150 mOsmol/Kg H2O.

In accordance with another embodiment of the invention, there is provided a pharmaceutical composition for nasal administration to humans, or to warm-blooded animals, comprising: (A) a therapeutically effective amount of insulin, (B) a permeation enhancer, (C) a liquid carrier, and (D) a combination of non-ionic surfactants; wherein the combination of non-ionic surfactants comprises: (i) at least one fatty acid ester of a sugar or sugar alcohol and (ii) at least one pegylated fatty acid ester of a sugar or sugar alcohol; and wherein the osmolality of the composition is <200 mOsmol/Kg H2O. Preferably the osmolality of the composition is <150 mOsmol/Kg H2O.

In accordance with another embodiment of the invention, there is provided a pharmaceutical composition for nasal administration to humans, or to warm-blooded animals, comprising: (A) a therapeutically effective amount of insulin, (B) a permeation enhancer, (C) a liquid carrier, and (D) a combination of non-ionic surfactants; wherein the combination of non-ionic surfactants comprises: (i) at least one fatty acid ester of a sugar or sugar alcohol and (ii) at least one pegylated fatty acid ester of a sugar or sugar alcohol; wherein the osmolality of the composition is <200 mOsmol/Kg H2O; and wherein the composition is at an acidic pH, but no greater than a pH of 4.5. Preferably the osmolality of the composition is <150 mOsmol/Kg H2O.

As known in the art "peg" is an abbreviation for polyethylene glycol or polyoxyethylene—polymeric forms of ethylene oxide—either of which may be produced synthetically or derived from animal or vegetable sources. As used hereinabove and hereinbelow, and as understood in the art, the term "pegylated" shall mean that a polyethylene glycol and/or polyoxyethylene chain(s) is covalently attached to a molecule. The pegylated portion of the fatty acid ester of the sugar or sugar alcohol of the present invention may include a polymer chain that includes from about 4 to about 25 oxyethylene units.

In one embodiment of the present invention, the pegylated portion of the fatty acid ester of the sugar or sugar alcohol includes a polymer chain that includes about 20 oxyethylene units.

Simple sugars include sucrose, fructose, glucose, galactose, maltose, lactose, and mannose. Fatty acids generally have from 12 to 20 carbon atoms and may be saturated or unsaturated. Common fatty acids include lauric acid, myristic acid, palmitic acid, stearic acid, linoleic acid, and oleic acid. As known in the art, sorbitol, derived from glucose by hydrogenation or electrolytic reduction, is a sugar alcohol. The Spang series of surfactants are esters of sorbitol and fatty acids, and are therefore fatty acid esters of sugar alcohols useful in the non-ionic surfactant combinations of the compositions of the instant invention. As known in the art sorbitan is produced through a dehydration process of sorbitol and this intermediate may be esterified with a fatty acid, whereby esters of sorbitan are included within the meaning of the term "fatty acid ester of a sugar or sugar alcohol" as it is used hereinabove and hereinbelow to describe that element of the instant invention. Pegylated sorbitan monolaurate (or polyoxyethylene sorbitan monolaurate) sometimes referred to as Polysorbate 20, is included within the meaning of the term "pegylated fatty acid ester of a sugar or sugar alcohol" as the term is used hereinabove and hereinbelow to describe that element of the instant invention. In one embodiment, the combination of non-ionic surfactants contains at least one fatty acid ester of a sugar alcohol and at least one pegylated fatty acid ester of a sugar alcohol. In one embodiment the sugar alcohol is sorbitol.

The esterified sugar or sugar alcohol may be esterified with one or more fatty acids, which may be the same or different. In one embodiment, the sugar or sugar alcohol is mono-esterifed.

In preferred embodiments of the invention, the combination of non-ionic surfactants, comprising (i) at least one fatty acid ester of a sugar or sugar alcohol and (ii) at least one pegylated fatty acid ester of a sugar or sugar alcohol, has a combined hydrophilic-lipophilic balance (HLB) of from about 7 to about 14.

In a particularly preferred embodiment of the invention, the combination of non-ionic surfactants, comprising (i) at least one fatty acid ester of a sugar or sugar alcohol and (ii) at least one pegylated fatty acid ester of a sugar or sugar alcohol, comprises Sorbitan Monolaurate and Polysorbate 20, respectively.

In one embodiment, the hereinabove-described and hereinbelow-described compositions of the invention are hypotonic relative to the red blood cells of the human body. In such an embodiment, in general, the osmolality of the composition is <200 mOsmol/Kg H2O. Preferably the osmolality of the composition is <150 mOsmol/Kg H2O. In an embodiment of the invention the osmolality of the composition is <30 mOsmol/Kg H2O. In another embodiment, the osmolality of the composition is about 25 mOsmol/Kg H2O.

In another embodiment, the invention further relates to treating a patient in need of insulin with any of the hereinabove described and hereinbelow described pharmaceutical compositions for nasal administration to humans, or to warm-blooded animals, which contain inter alia: insulin, a permeation enhancer, and a liquid carrier; wherein the composition further comprises a combination of non-ionic surfactants; wherein the combination of non-ionic surfactants comprises: (i) at least one fatty acid ester of a sugar or sugar alcohol and (ii) at least one pegylated fatty acid ester of a sugar or sugar alcohol.

The invention further relates to treating a patient in need of insulin by nasal administration of a composition, which contains inter alia: insulin, a permeation enhancer, and a liquid carrier; wherein the osmolality of the composition is <200 mOsmol/Kg H2O. Preferably the osmolality of the composition is <150 mOsmol/Kg H2O. In an embodiment of the invention the osmolality of the composition is <30 mOsmol/Kg H2O. In another embodiment of the invention the osmolality of the composition is about 25 mOsmol/Kg H2O.

The invention further relates to treating a patient in need of insulin with any of the hereinabove described and hereinbelow described pharmaceutical compositions for nasal administration to humans, or to warm-blooded animals, which contain inter alia: insulin, a permeation enhancer, and a liquid carrier; wherein the composition has an acidic pH of no greater than 4.5. Preferably the pH of the composition is no greater than 4 nor below 2. The pH is preferably at least 2.

The pH of the compositions may be maintained by the use of a suitable buffer. The selection of a buffer to maintain the desired pH is deemed to be within the scope of those skilled in the art based on the teachings set forth herein. As representative examples of suitable buffers there may be mentioned citric acid buffer, phosphate buffer, hydrochloric acid, hydrochloric acid and sodium hydroxide, and the like, as is in common use and also suitable for medical formulations. Preferred, however, are the use of monovalent inorganic acids and bases, i.e. hydrochloric acid or hydrobromic acid is the pH adjuster on the acidic side, and sodium or potassium hydroxide on the basic side, thus producing buffered solutions with insulin. According to the Lowry-Brønsted theory of acids and bases, insulin is the ampholyte providing the sink for the buffer to keep the pH within the desired range. In the preferred embodiments the acidic pH is maintained with hydrochloric acid, or with hydrochloric acid and sodium hydroxide; and is substantially free of citrates and phosphates. In such preferred embodiments the composition is substantially free of fibrilliform or beta-sheet insulin polymorphs.

In general, the permeation enhancer that is employed is one that enhances the permeation of the insulin composition through the membrane of a body cavity.

In general, the permeation enhancer that is employed is one that enhances the permeation of the insulin composition through the membrane of a body cavity and in particular through the nasal mucosa.

In a composition containing an effective amount of insulin a preferred permeation enhancer is a compound of the structure:

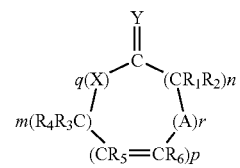

wherein X and Y are oxygen, sulfur or an imino group of the structure

or =N—R with the proviso that when Y is the imino group, X is an imino group, and when Y is sulfur, X is sulfur or an imino group, A is a group having the structure

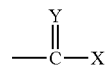

wherein X and Y are defined above, m and n are integers having a value from 1 to 20 and the sum of m+n is not greater than 25, p is an integer having a value of 0 or 1, q is an integer having a value of 0 or 1, r is an integer having a value of 0 or 1, and each of R, $R_1$, $R_2$, $R_3$, $R_4$, $R_5$ and $R_6$ is independently hydrogen or an alkyl group having from 1 to 6 carbon atoms which may be straight chained or branched provided that only one of $R_1$ to $R_6$ can be an alkyl group, with the proviso that when p, q and r have a value of 0 and Y is oxygen, m+n is at least 11, and with the further proviso that when X is an imino group, q is equal to 1, Y is oxygen, and p and r are 0, then m+n is at least 11, and said compound will enhance the rate of the passage of the drug across body membranes. Hereinafter these compounds are referred to as enhancers. When R, $R_1$, $R_2$, $R_3$, $R_4$, $R_5$ or $R_6$ is alkyl it may be methyl, ethyl, propyl, isopropyl, butyl, isobutyl, sec-butyl, amyl, hexyl, and the like. Such permeation enhancers are described in U.S. Pat. No. 5,023,252 and U.S. Pat. No. 5,731,303.

Preferably, the enhancer compounds of this invention are the cyclic lactones (the compounds wherein both X and Y are oxygen, (q is 1 and r is 0), the cyclic diesters (the compounds wherein both X and Y are oxygen, and both q and r are 1), and the cyclic ketones (the compounds wherein both q and r are 0 and Y is oxygen). In the cyclic diesters m+n is preferably at least 3. In the cyclic ketones m+n is preferably from 11 to 15 and p is preferably 0.

Enhancers of the above structural formula are referred to herein as "Hsieh enhancers" and are described, for example, in aforementioned U.S. Pat. Nos. 5,023,252 and 5,731,303 (hereinafter "Hsieh Patents"). Such enhancers are lipophilic and are "membrane-compatible," meaning that they do not cause damage to the membrane on which the composition of the present invention is to be applied (hereinafter "target membrane"). Such enhancers produce also a low level of irritability or no irritability to the target membrane and, in fact serve as an emollient.

Preferred enhancers for use in the present invention are macrocyclic enhancers. The term "macrocyclic" is used herein to refer to cyclic compounds having at least 12 carbons in the ring. Examples of preferred macrocyclic enhancers for use in the present invention include: (A) macrocyclic ketones, for example, 3 methylcyclopentadecanone (muscone), 9-cycloheptadecen-1-one (civetone), cyclohexadecanone, and cyclopentadecanone (normuscone); and (B) macrocyclic esters, for example, pentadecalactones such as oxacyclohexadecan-2-one (cyclopentadecanolide, (ω-pentadecalactone).

Oxacyclohexadecan-2-one and cyclopentadecanone are especially preferred.

Although the above are preferred permeation enhancers, one of ordinary skill in the art would recognize that the instant teachings would also be applicable to other permeation enhancers. Non-limiting examples of other permeation enhancers useful in the instant invention are the simple long chain esters that are Generally Recognized As Safe (GRAS) in the various pharmacopoeial compendia. These may include simple aliphatic, unsaturated or saturated (but preferably fully saturated) esters, which contain up to medium length chains. Non-limiting examples of such esters include isopropyl myristate, isopropyl palmitate, myristyl myristate, octyl palmitate, and the like. The enhancers are of a type that are suitable for use in a pharmaceutical composition. The artisan of ordinary skill will also appreciate that those materials that are incompatible with or irritating to mucous membranes should be avoided.

The enhancer is present in the composition in a concentration effective to enhance penetration of the insulin, to be delivered, through the membrane. Various considerations should be taken into account in determining the amount of enhancer to use. Such considerations include, for example, the amount of flux (rate of passage through the membrane) achieved and the stability and compatibility of the components in the formulations. The enhancer is generally used in an amount of about 0.01 to about 25 wt. % of the composition, more generally in an amount of about 0.1 to about 15 wt. % of the composition, and in preferred embodiments in an amount of about 0.5 to about 15 wt % of the composition.

The liquid carrier is present in the composition in a concentration effective to serve as a suitable vehicle for the compositions of the present invention. In general, the carrier is used in an amount of about 40 to about 98 wt. % of the composition and in preferred embodiments in an amount of about 50 to about 98 wt. % of the composition.

The insulin compositions of the present invention are preferably delivered as a nasal spray. In such an embodiment, the preferred liquid carrier is water with the insulin being dispersed or dissolved in the water in a therapeutically effective amount.

In one preferred embodiment, the permeation enhancer is emulsified in the aqueous phase that contains the insulin. The emulsification may be effected through the use of one or more suitable surfactants. The selection of a suitable surfactant is deemed to be within the scope of those skilled in the art based on the teachings herein. Essentially any suitable surfactant or mixture of surfactants can be used in the practice of the present invention, including, for example, anionic, cationic, and non-ionic surfactants. Preferred surfactants are non-ionic surfactants, with those having a hydrophilic-lipophilic balance (HLB) of from about 7 to about 14 being particularly preferred. Examples of such non-ionic surfactants are PEG-60 corn glycerides, PEG-20 sorbitan monostearate, phenoxypoly(ethyleneoxy)ethanol, sorbitan monooleate, and the like. Especially preferred are compendial surfactants such as those described in compendia such as the Food Chemicals Codex, National Formulary, U.S. Pharmacopeia, and the Code of Federal Regulations. It is preferred that the average diameter of the droplets of the emulsion be from about 500 mn to about 20 μm and more preferably from about 1 μm to about 10 μm. In general the surfactant is present in an amount no greater than about 2 wt. % of the composition and more generally no greater than about 0.5 wt. % of the composition.

In one preferred embodiment, the emulsified or discontinuous phase that contains the permeation enhancer is in the form of droplets. In general, smaller droplets confer greater stability. Larger droplets may cause instability and decrease shelf-life. In preferred embodiments the droplet size ranges from 0.1 microns to 20 microns and preferably from 0.1 microns to 5 microns.

In general compositions that contain insulin are stored in a refrigerator and such refrigeration may result in crystallization of the permeation inhibitor. In order to inhibit or prevent such crystallization, in a preferred embodiment the composition includes one or more crystallization inhibitors to inhibit the crystallization of the permeation enhancer. Crystallization, if allowed to proceed, renders the emulsion unstable and has an adverse effect on shelf life. Preferred crystallization inhibitors function by lowering the temperature at which the involved compound crystallizes. Examples of such crystallization inhibitors include natural oils, oily substances, waxes, esters, and hydrocarbons. Examples of natural oils or oily substances include Vitamin E acetate, octyl palmitate, sesame oil, soybean oil, safflower oil, avocado oil, palm oil, and cottonseed oil. The selection of a suitable crystallization inhibitor is deemed to be within the scope of those skilled in the art from the teachings herein. Preferred crystallization inhibitors function by lowering the temperature at which the permeation enhancer crystallizes.

Inhibitors which are capable of lowering the temperature of crystallization of the involved compound to below about 25° C. are particularly preferred, with those capable of lowering the crystallization of the involved compound to below about 5° C. being especially preferred. Examples of especially preferred crystallization inhibitors for use in inhibiting the crystallization of oxacyclohexadecan-2-one include hexadecane, isopropyl myristate, octyl palmitate, cottonseed oil, safflower oil, and Vitamin E acetate, each of which may be used in pharmaceutical preparations.

The crystallization inhibitor is present in the composition in a concentration effective to inhibit the crystallization of the permeation enhancer. In general the crystallization inhibitor is present in an amount of about 0.001 to about 5 wt. % of the composition, more generally in an amount of from about 0.01 to about 2 wt % of the composition. In one embodiment the crystallization inhibitor is present in an amount of from about 0.1 to about 1 wt. % of the composition. The crystallization inhibitor is one preferably used when the enhancer has a crystallization temperature above about 0 degrees Centigrade. In particular, for example, a crystallization inhibitor is preferably used when the enhancer is, pentadecalactone and/or cyclohexadecanone, since these crystallize above room temperature.

The composition of the present invention is generally delivered through a nasal spray applicator. If intra-nasal application is desired, the composition may be placed in an intra-nasal spray-dosing device or atomizer and be applied by spraying it into the nostrils of a patient for delivery to the mucous membrane of the nostrils. A sufficient amount is applied to achieve the desired systemic or localized drug levels. For an intra-nasal spray, up to about 200 microliters is typically applied, with an application of about 50 to about 150 microliters being preferred. One or more nostrils may be dosed and application may occur as often as desired or as often as is necessary. In preferred embodiments, the nasal spray applicator is selected to provide droplets of the composition of a mean size of from about 10 microns to about 200 microns. More generally the droplet size is from about 30 microns to about 100 microns.

The insulin spray composition of the invention is generally employed in a dosing regimen that is dependent on the patient being treated. Thus the frequency of the use and the amount of the dose may vary from patient to patient. In general, dosing is in an amount (the amount internalized after absorption from the mucosa) of from about 3 IU to about 15 IU and the frequency of dose is 3 to 4 times per day. As known in the art, the treatment of a disease such as diabetes through insulin therapy varies from patient to patient, and based on known insulin therapy and the teachings herein one skilled in the art can select the dosing regimen and dosage for a particular patient or patients.

The composition of the present invention comprises insulin. The insulin is present in the composition in a therapeutically-effective amount. In general the insulin is present in an amount of about 0.01 to about 15 wt. % of the composition, more generally an amount of about 0.01 to about 10 wt. % of the composition. In one embodiment the insulin is present in an amount of about 0.1 to about 5 wt. % of the composition.

Although a preferred embodiment is a preformulated composition, it is also within the scope of the present invention that a patient may be treated with the hereinabove described combination that is not preformulated; i.e., the insulin in liquid carrier and the enhancer may be mixed at the time of application, such as where the mixing occurs in an atomizer at the time the composition is sprayed.

The Examples illustrate preferred embodiments of the invention and are not to be regarded as limiting.

EXAMPLE 1

Four separate aqueuos insulin emulsions (formulations A, B, C, and D) are prepared according to the formulations described in the table below. Component CPE-215 is the Applicant's proprietary compound and is also known as Cyclopentadecanolide; it facilitates the migration of insulin through the nasal mucosa.

Insulin Formulation for Pig Experiment

| Reagents: | Code: A % | B % | C % | D % |
|---|---|---|---|---|
| Insulin | 0.1 | 1.0 | 1.0 | 1.0 |
| CPE-215 | — | 2.0 | 2.0 | 2.0 |

Insulin Formulation for Pig Experiment

| Reagents: | Code: A % | B % | C % | D % |
|---|---|---|---|---|
| Cottonseed Oil | — | 1.0 | 1.0 | 0.7 |
| Glycerin | — | — | — | 2.0 |
| Sorbitan Laurate (a.k.a. Crill 1; a surfactant) | — | 0.6 | 0.6 | — |
| Polysorbate 20 (a.k.a. Crillet 1; a surfactant) | — | 0.7 | 0.7 | — |
| Pemulen TR2 | — | — | — | 0.1 |
| H2O | 99.1 | 94.3 | 93.2 | 93.7 |
| TEA | — | — | — | 0.5 |
| HCl (5N) | — | — | 0.2 | — |
| NaOH (1N) | — | — | 1.3 | — |
| Citric Acid (1 H2O) | 0.6 | 0.3 | — | — |
| Sodium Citrate (2 H2O) | 0.2 | 0.1 | — | — |
| Benzalkonium chloride | — | — | — | 0.003 |
| | 100 | 100 | 100 | 100 |
| pH: | 3.19 | 3.53 | 7.32 | 8.07 |

EXAMPLE 2

C-peptide blood levels can indicate whether or not a person is producing insulin and approximately how much. Insulin is initially synthesized in the pancreas as proinsulin. In this form the alpha and beta chains of active insulin are linked by a third polypeptide chain called the connecting peptide, or C-peptide, for short. Because both insulin and C-peptide molecules are secreted, for every molecule of insulin in the blood, there is one of C-peptide. Therefore, levels of C-peptide in the blood can be measured and used as an indicator of insulin production in those cases where exogenous insulin (from injection) is present and mixed with endogenous insulin (that produced by the body) a situation that would make meaningless a measurement of insulin itself. The C-peptide test can also be used to help assess if high blood glucose is due to reduced insulin production or to reduced glucose intake by the cells. There is little or no C-peptide in the blood of type 1 diabetic humans, and C-peptide levels in type 2 diabetics can be reduced or normal. The concentrations of C-peptide in non-diabetics are on the order of 0.5-3.0 ng/ml.

An evaluation of the compositions of this invention was carried out in vivo as described below.

Pharmacokinetics and Pharmacodynamics in Yucatan Minipigs of Intranasal CPE-215/Insulin Formulations This study was performed in accordance with the NIH "Guide For the Care and Use of Laboratory Animals" and the Federal Animal Welfare Act, and followed a protocol approved by the University of New Hampshire Institutional Animal Care and Use Committee. This study's objective was to evaluate and characterize the pharmacokinetic and pharmacodynamic effectiveness of insulin formulations after intranasal delivery to Yucatan minipigs.

Previously, it had been determined, in beagles (Hseih, 1993), that Cyclopentadecanolide facilitates the migration of insulin through the nasal mucosa. In order to verify this in minipigs, as a step toward evaluation in human volunteers, formulations were assessed for insulin blood levels and glucodynamics.

Materials, Methods, and Formulations

The formulations tested were aqueous insulin emulsions, containing pharmaceutical grade human recombinant insulin, obtained from Diosynth, Inc., a division of Akzo Nobel, Inc. These formulations varied slightly in composition; however, each contained insulin at 1% w/w, and CPE-215 at 2% w/w. These formulations were dispensed from intranasal atomizers, developed for humans by Valois of America. Two puffs of 100 microliters each were dispensed to pigs that had previously been cannulated with an indwelling jugular catheter. Each 100 microliter spray dispensed 1 milligram, or approximately 25 IU of insulin. An extension to the actuator was used, provided also by Valois of America, the need for which (to deliver formulation to the absorptive surface of the vestibule and labyrinthine turbinate region) was determined in a preliminary pilot study. The same actuator, dispensing 100 microliters, was used with the extension attached. These intranasally delivered doses were compared to three units of insulin administered subcutaneously (SQ) as a positive control.

Animal Protocol

Four female Yucatan miniature swine (pigs) were purchased from the UNH Miniature Swine Research Farm. During the study, the pigs were housed in an environmentally controlled research animal room (temperature 25+/-2 C and 12 hour light/dark cycle), fed commercial research pig chow, and had free access to water at all times. The pigs were 21 week-old Yucatan females:

Pig #1, Tag 121-5; Weight at start of study: 16.8 kg; DOB Nov. 26, 2002

Pig #2, Tag 121-4; Weight at start of study: 22.3 kg; DOB Nov. 26, 2002 (Note: #1 and #2 are littermates]

Pig #3, Tag 122-7; Weight at start of study: 18.3 kg; DOB Dec. 1, 2002

Pig #4, Tag 122-9; Weight at start of study: 15.5 kg; DOB Dec. 1, 2002 [Note: #3 and #4 are littermates].

Catheterization Methodology

The animals were prepared for the study with the surgical implantation of a jugular catheter 4 to 6 days before the study start. After heavy sedation with an intramuscular dose of xylazine and ketamine, the animals were masked down and maintained to effect deep surgical anesthesia with inhalation of isofluorane anesthetic and oxygen. With the animals in dorsal recumbency, a skin incision was made in the right jugular furrow and followed by blunt dissection of the subcutaneous and perivascular connective tissues to expose the right jugular vein cranial to the thoracic inlet. A length of 0.050 inch bore Tygon® intravenous catheter tubing was inserted through a small incision in the clamped vein and positioned caudally into the anterior vena cava (approximately 12 to 15 cm from the jugular incision). The catheter was transfixed to the vein and deep subcutaneous tissues suture. The jugular vein cranial to the catheter was ligated with polypropylene suture. The free end of the catheter was routed by blunt dissection through the subcutis to the interscapular dorsum, pulled through a small skin incision, and transfixed to the skin with polypropylene suture. The catheter was capped with a syringe docking device and filled with an anti-thrombotic preparation. The antithrombotic consisted of 60% (w/v) polyvinylpyrrolidone (10,000 mw, PVP-10) and physiologic saline/sodium heparin (50,000 units of heparin per 100 mL). The subcutis and skin incision in the jugular furrow were closed with synthetic absorbable and polypropylene sutures, respectively. The animals were comfortably bandaged to protect the catheter and skin incision and covered with a vest made for dog catheter work. Intramuscular butorphanol was administered as an analgesic immediately and 12 hours after surgery.

Study Design

At the time of dosing, the pigs were restrained in a cloth sling. The pigs were afterwards free to move about their respective individual pens and were only temporarily restrained in close quarters at the front of the pen with a movable wooden gate at the time of blood sampling. Each pig was dosed twice with each of the four different formulations over a two week period with at least 18 hours between treatments. The intranasal dosing (Formulation B, C, D) entailed dispensing 100 µL of a 1% insulin emulsion through an aerosol doser (human type intranasal actuator), once per each nostril (Total dose 50 IU), or subcutaneous dosing (Formulation A), 120 0 µL of a 0.1% buffered sterile solution using a 1 cc sterile syringe (3 IU) equipped with a 22 ga. needle. Dosing intervals between pigs was timed, and was approximately five minutes.

Baseline venous blood specimens were collected just prior to intranasal or SQ insulin administration, and blood was thereafter sampled at 0 (just before treatment), 15, 30, 45, 60, 90, 120, and 180 minutes after application. Bleeding was approximately five minutes apart between pigs, the interval adjusted relative to the dosing time within one minute of target time. Each pig was monitored with a hand-held commercial glucometer at each blood collection time to ensure animal wellness.

The blood was collected into sodium heparinized glass tubes. The plasma was retrieved and stored at −20° C. until analyzed for insulin, C-peptide, and glucose. There were eight days of treatment, with each of the four pigs treated each day. Pigs were crossed over (two successive identical latin squares) with each pig receiving a different treatment each day, according to the following schedule:

Treatment Schedule

| D = Day | P = Pig | Treatments |
|---|---|---|
| D1 = Mar. 25, 2003 | P1 = Pig 121-5 | A = Subcutaneous 120 µL (3IU) |
| D2 = Mar. 26, 2003 | P2 = Pig 121-4 | B = IN Form. 013-44-2 pH 3.5 |
| D3 = Mar. 27, 2003 | P3 = Pig 122-7 | C = IN Form. 013-44-3 pH 7.32 |
| D4 = Mar. 28, 2003 | P4 = Pig 122-9 | D = IN Form. 013-45 pH 8.0 |
| D5 = Apr. 1, 2003 | | |
| D6 = Apr. 2, 2003 | | |
| D7 = Apr. 3, 2003 | | |
| D8 = Apr. 4, 2003 | | |

Treatments/Days

| Day | Pig 1 | Pig 2 | Pig 3 | Pig 4 |
|---|---|---|---|---|
| 1 | A | B | C | D |
| 2 | B | C | D | A |
| 3 | C | D | A | B |
| 4 | D | A | B | C |
| 5 | A | B | C | D |
| 6 | B | C | D | A |
| 7 | C | D | A | B |
| 8 | D | A | B | C |

Sample Collection and Assay Methods

Heparinized plasma was analyzed for insulin concentration using a commercial RIA assay for insulin (Linco research, Inc.; Human Insulin Specific RIS Kit, Cat#HI- 14K). Insulin was reported in micro International Units)/milliliter of plasma (µU/mL). C-Peptide was analyzed with a commercial kit specific for porcine C-Peptide (Linco research, Inc.; Porcine C-Peptide RIA Kit, Cat#PCP-22K) and reported in units of ng/mL.

Glucose was measured at the time of collection using a Glucometer (Lifescan (J&J) One Touch Fast Take™), and in the laboratory using a commercial enzymatic assay (Sigma Diagnostics, Procedure 315) and was measured in mg/dL.
Deviation from Protocol There were no deviations from protocol.

BRIEF DESCRIPTION OF THE SEVERAL VIEWS OF THE DRAWINGS

Results for Glucose

The results showed good reduction in blood glucose values, as measured in blood by the hexokinase enzymatic method, and are historically commensurate for this positive control, SQ insulin; the SQ dose reached a minimum glucose level at an average of 30 minutes Post Rx. For intranasal Formulation B, excellent glucodynamic reduction was seen with a more rapid onset, 15 minutes or faster to trough, but of shorter duration (90-120 min.) than SQ (180 min.). Formulation C had a similar rapid onset to B, but of less magnitude. Formulation D was devoid of appreciable glucodynamic activity. The reproducibility, both intradose and day to day, was good (no variances of any treatment differed significantly, P<0.05). (See FIG. 1)

The enzymatic glucose assay correlated well with the corresponding glucometer results performed at the time of blood collection (r=0.9575; p<0.0001).
Results for Insulin The results showed good insulin blood levels for the Formulation A, SQ positive control, with the average value peaking at 15 minutes with an average $C_{max}$ of 59.85 µU/mL. (See FIG. 2).

Formulation B showed much higher blood levels than any other formulation, peaking at 15 minutes with an average $C_{max}$ of 182.4 µU/mL. (See FIG. 2).

Formulation C showed lower blood levels than either A or B, indicating reduced delivery of insulin at physiological pH compared with the acidic form, having a $C_{max}$ of 64.59 µU/mL at 15 minutes. (See FIG. 2).

Formulation D showed little change over fasted baseline levels. No $C_{max}$ was observed. (See FIG. 2).
Results for C-Peptide C-Peptide for fasted, untreated animals (time zero) averaged 0.35 ng/mL (n=36). The onset of action of the four treatments was similar to the respective curves obtained for the glucodynamics. Treatment B has a faster onset of depression of C-Peptide, followed by A, then C, then D. Treatment A had the longest depression of C-Peptide, approximately 3 hours, whereas the other treatments had normal levels by this time, reflecting resumption of endogenous insulin production.

EXAMPLE 3

The following composition may also be prepared:

| Component | % w/w | Content per 100 µl Dose in mg |
|---|---|---|
| Recombinant Human Insulin | 1 | 1.0 |
| Pentadecalactone | 2 | 2.0 |
| Cottonseed oil | 1 | 1.0 |
| Sorbitan Monolaurate (Span ® 20) | 0.6 | 0.6 |
| Polysorbate 20 (Tween ® 20) | 0.7 | 0.7 |
| Hydrochloric acid | | As Needed to Achieve a Ph of about 3.5 |
| Sodium Hydroxide | | As Needed to Achieve a Ph of about 3.5 |
| Sterile Water for Injection | | q.s. |

We claim:

1. A pharmaceutical composition for nasal administration to humans, or to warm-blooded animals, comprising: (A) a therapeutically effective amount of insulin, (B) a permeation enhancer, (C) a liquid carrier, and (D) a combination of non-ionic surfactants; wherein the combination of non-ionic surfactants comprises: (i) at least one fatty acid ester of a sugar or sugar alcohol and (ii) at least one pegylated fatty acid ester of a sugar or sugar alcohol, wherein the composition is at an acidic pH, but no greater than a pH of 4.5.

2. The pharmaceutical composition of claim 1, wherein said combination of non-ionic surfactants, comprising (i) at least one fatty acid ester of a sugar or sugar alcohol and (ii) at least one pegylated fatty acid ester of a sugar or sugar alcohol, has a combined hydrophilic-lipophilic balance (HLB) of from about 7 to about 14.

3. The pharmaceutical composition of claim 1, wherein the osmolality of the composition is <200 mOsmol/Kg H2O.

4. The pharmaceutical composition of claim 3, wherein said combination of non-ionic surfactants, comprising (i) at least one fatty acid ester of a sugar or sugar alcohol and (ii) at least one pegylated fatty acid ester of a sugar or sugar alcohol, has a combined hydrophilic-lipophilic balance (HLB) of from about 7 to about 14.

5. The pharmaceutical composition of claim 1, wherein the osmolality of the composition is <150 mOsmol/Kg H2O.

6. The pharmaceutical composition of claim 1, wherein the osmolality of the composition is <30 mOsmol/Kg H2O.

7. A method for treating a patient with insulin comprising nasally administering to a patient in need of insulin treatment the composition of claim 1.

8. A method for treating a patient with insulin comprising nasally administering to a patient in need of insulin treatment the composition of claim 2.

9. A method for treating a patient with insulin comprising nasally administering to a patient in need of insulin treatment the composition of claim 3.

10. A method for treating a patient with insulin comprising nasally administering to a patient in need of insulin treatment the composition of claim 4.

11. A method for treating a patient with insulin comprising nasally administering to a patient in need of insulin treatment the composition of claim 5.

12. A method for treating a patient with insulin comprising nasally administering to a patient in need of insulin treatment the composition of claim 6.

* * * * *